(12) United States Patent
Kawano et al.

(10) Patent No.: US 7,268,938 B2
(45) Date of Patent: Sep. 11, 2007

(54) IN-VIVO EXAMINATION APPARATUS

(75) Inventors: Yoshihiro Kawano, Hachioji (JP);
Kenichi Koyama, Sagamihara (JP);
Atsuhiro Tsuchiya, Hachioji (JP)

(73) Assignee: Olympus Coporation, Tokyo (JP)

( * ) Notice: Subject to any disclaimer, the term of this patent is extended or adjusted under 35 U.S.C. 154(b) by 0 days.

(21) Appl. No.: 11/095,518

(22) Filed: Apr. 1, 2005

(65) Prior Publication Data

US 2005/0237604 A1 Oct. 27, 2005

(30) Foreign Application Priority Data

Apr. 7, 2004 (JP) ............................. 2004-113155
Jul. 29, 2004 (JP) ............................. 2004-221565

(51) Int. Cl.
*G02B 21/00* (2006.01)
*G02B 21/06* (2006.01)
(52) U.S. Cl. ...................... 359/368; 359/384; 359/385; 601/4
(58) Field of Classification Search ........ 359/368–398; 351/200–247
See application file for complete search history.

(56) References Cited

U.S. PATENT DOCUMENTS

| | | | |
|---|---|---|---|
| 4,290,666 A * | 9/1981 | Rudel ......................... 359/503 |
| 5,065,741 A * | 11/1991 | Uchiyama et al. ............. 601/4 |
| 5,748,366 A * | 5/1998 | Yasunaga et al. ........... 359/368 |
| 6,543,914 B2 * | 4/2003 | Sander ....................... 362/401 |
| 6,690,510 B2 * | 2/2004 | Kanao ........................ 359/380 |
| 6,781,752 B2 * | 8/2004 | Engelhardt et al. ......... 359/385 |
| 6,947,211 B2 * | 9/2005 | Metelski ..................... 359/384 |
| 6,999,554 B2 * | 2/2006 | Mertelmeier ................. 378/37 |

FOREIGN PATENT DOCUMENTS

JP 2003-322803 11/2003

\* cited by examiner

*Primary Examiner*—Thong Q Nguyen
(74) *Attorney, Agent, or Firm*—Kenyon & Kenyon LLP (57) ABSTRACT

An in-vivo examination apparatus in which the examination angle can be changed while keeping an examination site in focus to carry out accurate in-vivo examination is provided. The in-vivo examination apparatus includes a stage on which a living organism is mounted, a measurement head that irradiates the living organism on the stage with light emitted from a light source and detects light returning from the living organism, and a rotation mechanism that rotates the measurement head about a fixed point on the stage.

8 Claims, 10 Drawing Sheets

IN-VIVO EXAMINATION APPARATUS

BACKGROUND OF THE INVENTION

1. Field of the Invention

The present invention relates to an in-vivo examination apparatus.

2. Description of Related Art

In the related art, one example of an examination apparatus for carrying out in-vivo examination is disclosed in Japanese Unexamined Patent Application Publication No. 2003-322803 (see FIG. 1, etc. therein).

This examination apparatus, which is a microscope for surgical operations, has a microscope apparatus provided at the end of an articulated arm. By changing the rotation angle of each joint in the articulated arm, the position and orientation of the microscope apparatus can be freely adjusted, which allows it to be positioned close to the subject from any direction and magnified examination carried out.

While the examination apparatus disclosed in Japanese Unexamined Patent Application Publication No. 2003-322803 is sufficient for carrying out magnified examination of a subject during a surgical operation, it is not required to carry out examination from different angles while keeping the examination site at the focal point of the microscope apparatus. Therefore, in examining a previously focused examination site from different directions, this apparatus suffers from the disadvantage that a re-focusing operation must be carried out after the examination angle is changed.

BRIEF SUMMARY OF THE INVENTION

In light of the situation described above, it is an object of the present invention to provide an in-vivo examination apparatus that can change the examination angle while keeping the examination site in focus and that can carry out in-vivo examination with superior accuracy.

In order to achieve the object described above, the present invention provides the following features.

According to a first aspect, the present invention provides an in-vivo examination apparatus including a stage on which a living organism is mounted; a measurement head that irradiates the living organism on the stage with light emitted from a light source; and a rotation mechanism that rotates the measurement head about a fixed point on the stage.

In the above-described aspect, the rotation mechanism may have an operating region such that the measurement head can be positioned above and below the stage. Positioning the measurement head above the stage using the rotation mechanism allows the living organism to be examined from above, and the same living organism can be examined from below by positioning the measurement head below the stage. Preferably in the above-described aspect, the stage is formed of a transparent material.

In the above-described aspect, the rotation mechanism preferably includes a rotating arm that is rotatable about a horizontal axis, and wherein a driving mechanism for moving the measurement head along the radial direction may be provided on the rotating arm.

The invention according to the above-described aspect may also include a stage rotating mechanism for rotating the stage about a vertical axis.

The invention according to the above-described aspect may also include a stage raising/lowering mechanism for raising and lowering the stage in the vertical direction.

In the above-described aspect, the rotation mechanism may include an arc-shaped track centered on the focal position, and a slider that is moveable along the arc-shaped track. The measurement head may be attached to the slider.

The above-described aspect of the invention may also include a track rotating mechanism that rotates the arc-shaped track about a horizontal axis passing through a focal position of the measurement head.

The invention according to the above-described aspect may also include an externally provided light source, and an optical fiber for carrying light emitted from the light source to the measurement head. In addition, the measurement head may include an optical scanning unit for scanning the light from the light source and an objective optical system that images the light scanned by the optical scanning unit onto the stage.

In the above-described aspect, the fixed point is preferably arranged so as to be coincident with the focal position. Also, the stage is preferably moveable horizontally.

According to the first aspect of the invention, the measurement head can be rotated with respect to the living organism on the stage to allow examination from any direction. Also, since the examination angle is set with the measurement head using only the rotation mechanism, the examination direction can be changed while maintaining the accuracy of the examination site. Furthermore, since the examination angle is set with the measurement head using only the rotation mechanism, once the examination angle is set, an advantage is afforded in that it is possible to perform re-examination from the same angle with high accuracy.

According to a second aspect, the present invention provides an in-vivo examination apparatus including a stage on which a living organism is mounted; a measurement head having an objective lens that irradiates the living organism on the stage with light emitted from a light source, and that receives return light from the living organism; and a rotation mechanism that rotates the measurement head about a horizontal axis centered on a focal position of the objective lens. The rotation mechanism has at least three operating axes in a plurality of directions, in which the measurement head can move, and a control apparatus for engaging these operating axes.

According to this aspect, examination of a living organism can be carried out by focusing the objective lens at the end of the measurement head on the living organism mounted on the stage, irradiating the living organism with light emitted from the light source, and detecting light returning from the living organism. Then, to examine the living organism from different directions, the measurement head is rotated about the focal position of the objective lens by operating the rotation mechanism. Therefore, it is possible to change the viewing angle of the living organism while keeping the examination site in focus.

In the above-described aspect, the rotation mechanism preferably includes a rotating member that rotates about a horizontal axis away from the focal position of the objective lens; and a two-axis linear motion mechanism that can move the measurement head, which is attached to the rotating member, in two mutually orthogonal directions within a plane perpendicular to the rotating member. In addition, the control apparatus may control the two-axis linear motion mechanism in response to a rotation angle of the rotating member.

In the above-described aspect, the stage may be arranged so as to be rotatable about a vertical axis that intersects the focal position of the objective lens. By rotating the stage about a vertical axis, it is possible to rotate the measurement head within different vertical planes with respect to the living organism, which allows the examination region to be widened further.

In the above-described aspect, the measurement head may include an objective switching mechanism for switching between a plurality of objective lenses with different focal positions. In addition, the control apparatus may engage the operating axis based on information of the focal position of the objective lens, which is obtained from the objective switching mechanism.

According to the above-described second aspect of the invention, the measurement head can be rotated with respect to the living organism on the stage, which allows examination from a desired direction. Also, since the examination angle of the measurement head can be changed by the control apparatus without moving the focal position of the objective lens, it is possible to change the examination direction while maintaining the accuracy of the examination site. In this case, it becomes easy to secure the living organism to the stage since there is no need to align the center of rotation of the rotation mechanism with the center of rotation of the operating axes.

According to this aspect, examination of a living organism can be carried out by focusing the objective lens at the end of the measurement head on the living organism mounted on the stage, irradiating the living organism with light emitted from the light source, and detecting light returning from the living organism. Then, to examine the living organism from different directions, the measurement head is rotated about the focal position of the objective lens by operating the rotation mechanism. Therefore, it is possible to change the viewing angle of the living organism while keeping the examination site in focus.

In this case, since the control apparatus drives three or more operating axes, it is possible to change the angle of the measurement head within a vertical plane without moving the focal position thereof, regardless of which point the focal position of the objective lens is set to. Therefore, securing the living organism to the stage can be performed simply, without the need to consider the focal position.

In the above-described aspect, the rotation mechanism preferably includes a rotating member that rotates about a horizontal axis away from the focal position of the objective lens; and a two-axis linear motion mechanism that can move the measurement head, which is attached to the rotating member, in two mutually orthogonal directions within a plane perpendicular to the rotating member. In addition, the control apparatus may control the two-axis linear motion mechanism in response to a rotation angle of the rotating member.

By rotating the rotating member about a horizontal axis away from the focal position of the objective lens, any misalignment in the focal position of the objective lens can be corrected by operating the two-axis linear motion mechanism, and the angle of the measurement head can be changed within a vertical plane while keeping the focal position of the objective lens fixed. Reducing the number of rotation axes and performing correction with the linear motion axes allows the focal position to be fixed with better accuracy.

In the above-described aspect, the stage may be arranged so as to be rotatable about a vertical axis that intersects the focal position of the objective lens. By rotating the stage about a vertical axis, it is possible to rotate the measurement head within different vertical planes with respect to the living organism, which allows the examination region to be widened further.

In the above-described aspect, the measurement head may include an objective switching mechanism for switching between a plurality of objective lenses with different focal positions. In addition, the control apparatus may engage the operating axis based on information of the focal position of the objective lens, which is obtained from the objective switching mechanism.

By doing so, it is possible to examine the same living organism with multiple objective lenses having different magnifications.

According to the above-described second aspect of the invention, the measurement head can be rotated with respect to the living organism on the stage, which allows examination from a desired direction. Also, since the examination angle of the measurement head can be changed by the control apparatus without moving the focal position of the objective lens, it is possible to change the examination direction while maintaining the accuracy of the examination site. In this case, it becomes easy to secure the living organism to the stage since there is no need to align the center of rotation of the rotation mechanism with the center of rotation of the operating axes.

DETAILED DESCRIPTION OF THE INVENTION

FIRST EMBODIMENT

An in-vivo examination apparatus according to a first embodiment of the present invention is described below with reference to FIGS. 1 and 2.

Figure 1:
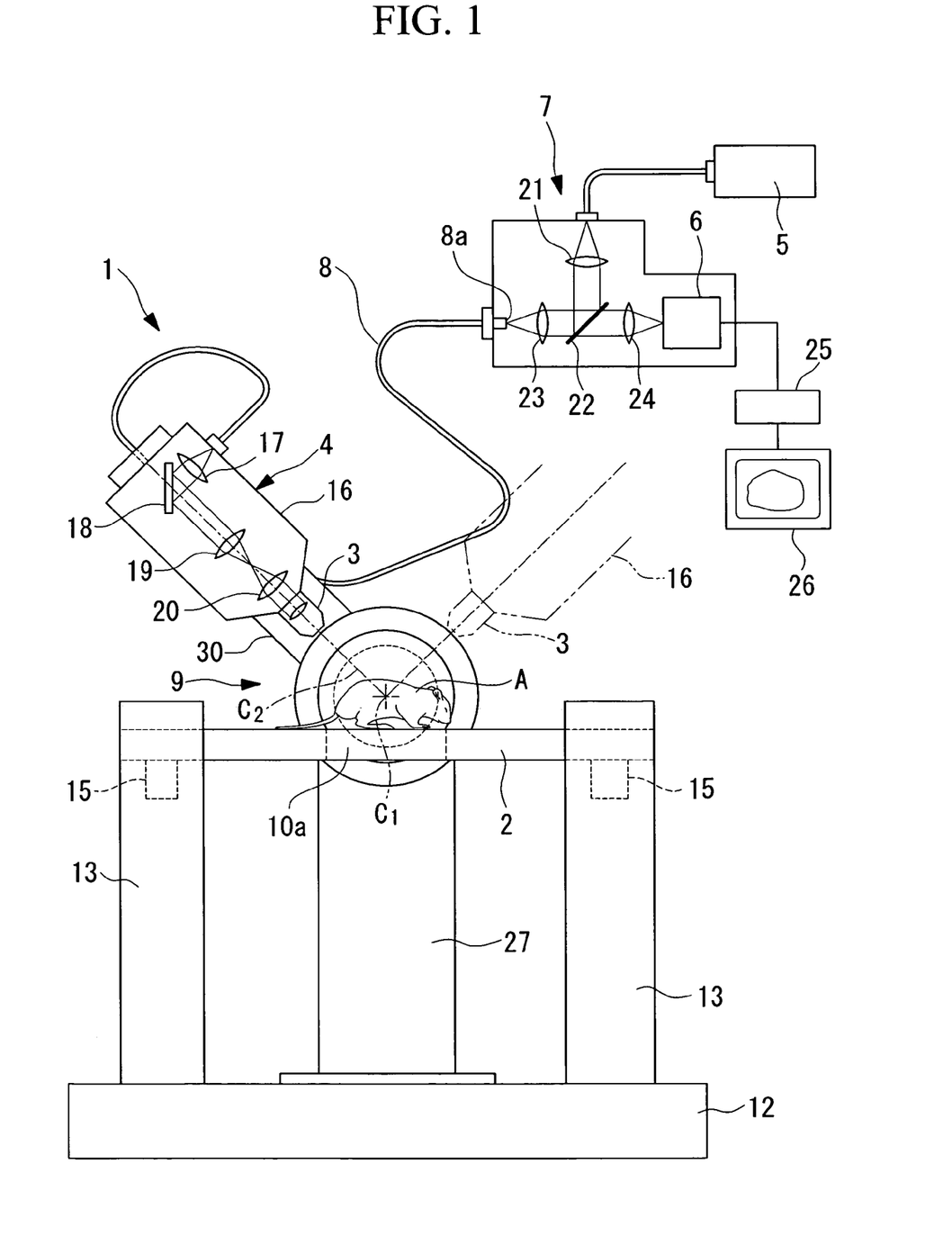
FIG. 1 is a front elevation view showing an in-vivo examination apparatus according to a first embodiment of the present invention.
Figure 2:
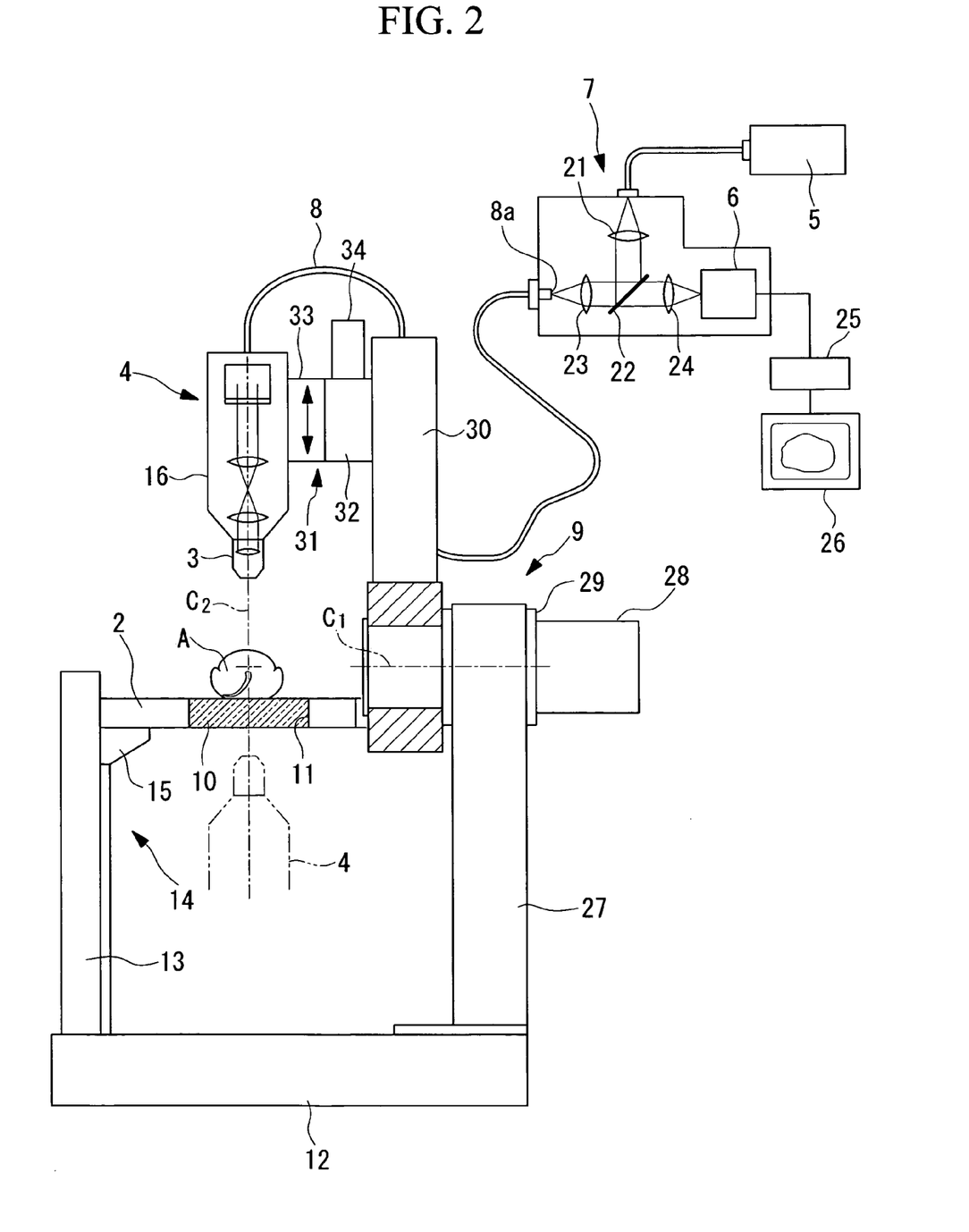
FIG. 2 is a side view showing the in-vivo examination apparatus in FIG. 1.

As shown in FIG. 1, an in-vivo examination apparatus 1 according to this embodiment includes a stage 2 on which a living organism A is mounted, a measurement head 4 having an objective optical system 3 disposed at the end thereof, an optical unit 7 having a light source 5 and a photodetector 6, an optical fiber 8 that connects the measurement head 4 and the optical unit 7, and a rotation mechanism 9 that rotates the measurement head 4.

The stage 2 is disposed horizontally, and a transparent part 10 made of a transparent material is provided substantially at the center thereof where the living organism A is mounted. As shown in FIG. 2, the transparent part 10 is disposed in a through-hole 11 that penetrates the stage 2 in the thickness direction thereof; this configuration allows light radiated from above to be transmitted and also allows examination from below the living organism A mounted on the transparent part 10.

The stage 2 is supported by a stage raising/lowering mechanism 14 that raises and lowers the stage 2 along a stand 13 provided on a base 12. The stage raising/lowering mechanism 14 supports the stage 2 and includes a raising/lowering slider 15 that is raised and lowered by an optional linear motion mechanism (not shown). By raising and lowering the raising/lowering slider 15 by operating the stage raising/lowering mechanism 14, the stage 2 can move the mounted living organism A upwards and downwards while keeping it horizontal.

The measurement head 4 includes a collimator optical system 17, an optical scanning unit 18, a pupil projection optical system 19, and an imaging optical system 20 inside a casing 16 having the objective optical system 3 at the end thereof. The collimator optical system 17 converts the laser light carried by the optical fiber 8 into a collimated beam. Although the optical scanning unit 18 is shown only schematically in the figure, by oscillating two galvano mirrors about two orthogonal axes, for example, it is possible to two-dimensionally scan the collimated beam from the collimator optical system 17.

The pupil projection optical system 19 focuses the laser light scanned by the optical scanning unit 18 to form an intermediate image. The imaging optical system 20 focuses the laser light forming the intermediate image to convert it to a collimated beam.

The objective optical system 3 is disposed close to the living organism A mounted on the stage 2, and focuses the collimated beam from the imaging optical system 20 to re-image it at a focal position set at the surface of the living organism A or inside the living organism A.

The optical unit 7 includes a collimator lens 21 for converting the laser light emitted from the laser light source 5 into a collimated beam, a dichroic mirror 22 that reflects the laser light and transmits return light returning to the optical unit 7, a focusing lens 23 that focuses the laser light reflected by the dichroic mirror 22 onto an end face 8*a* of the optical fiber 8, and a focusing lens 24 for focusing the return light transmitted through the dichroic mirror 22 onto the photodetector 6. The photodetector 6 is, for example, a photomultiplier tube. A monitor 26 is connected to the photodetector 6 via an image processing unit 25, and acquired images are displayed on the monitor 26.

The optical fiber 8, which is connected to the optical unit 7 and the measurement head 4, carries the laser light coming from the optical unit 7 and introduces it to the measurement head 4. Also, the optical fiber 8 carries return light returning from the measurement head 4 and introduces it into the optical unit 7. As shown in FIG. 2, the optical fiber 8 is guided through a rotating arm (to be described later) towards the inner side in the longitudinal direction and is lead out from near the center of rotation of the rotating arm to be connected to the external optical unit 7.

The rotation mechanism 9 includes a support member 27 fixed to the base 12, a motor 28 and a gear mechanism 29 fixed to the support member 27, and a rotating arm 30 fixed to the gear mechanism 29. The motor 28 and the gear mechanism 29 are fixed to the support member 27 with the rotation axis C1 thereof horizontal. The rotation axis C1 is disposed so as to intersect a position above the upper surface of the transparent part 10, close to the center of the transparent part 10 of the stage 2.

A linear motion mechanism 31 to which the measurement head 4 is attached is provided at one side of the rotating arm 30. The linear motion mechanism 31 includes a linear guide 32 fixed along the longitudinal direction of the rotating arm 30, a slider 33 supported so as to be moveable in a straight line in the longitudinal direction of the rotating arm 30 by means of the linear guide 32, and a motor 34 for driving the linear guide 32. The measurement head 4 is fixed to the slider 33 so that the objective optical system 3 thereof points towards the center of rotation of the rotating arm 30.

The operation of the in-vivo examination apparatus 1 according to this embodiment, configured in this way, will be described below.

As shown in FIG. 1, when using the in-vivo examination apparatus 1 according to this embodiment to carry out in-vivo examination of a living organism A, the living organism A is secured on top of the transparent part 10 of the stage 2. Then, by operating the linear motion mechanism 31 attached to the rotating arm 30, the measurement head 4 is moved in the outer radial direction along the longitudinal direction of the arm 30. By doing so, since a sufficiently large space can be ensured around the stage 2, the living organism A can be easily set in place.

Then, by operating the stage raising/lowering mechanism 14, the stage 2 on which the living organism A is mounted is raised and lowered, thus moving the living organism A so that the rotation axis C1 of the rotation mechanism 9 is placed at a position where it intersects the examination site of the living organism A.

Next, by operating the rotation mechanism 9, the rotating arm 30 and the measurement head 4 attached to the rotating arm 30 are rotated about the rotation axis C1. Accordingly, the tilt angle of the optical axis C2 of the measurement head 4 can be adjusted within a vertical plane, which allows measurement at a desired examination angle. In this state, by operating the linear motion mechanism 31 attached to the rotating arm 30, the measurement head 4 moves in the longitudinal direction of the rotating arm 30, that is, in the radial direction, and the distance between the living organism A and the objective optical system 3 at the end of the measurement head 4 is adjusted.

After setting it roughly by visual observation, the distance between the living organism A and the objective optical system 3 is set by operating the optical unit 7 while observing the monitor.

When the optical unit 7 is operated to emit laser light from the laser light source 5, the emitted laser light passes through the collimator lens 21 and the dichroic mirror 22 and is focused onto the end face 8*a* of the optical fiber 8 by the focusing lens 23 to be introduced into the optical fiber 8. The laser light introduced into the optical fiber 8 propagates through the optical fiber 8 and is guided to the measurement head 4. It then passes through the collimator optical system 17, the optical scanning unit 18, the pupil projection optical system 19, the imaging optical system 20, and the objective optical system 3 to be imaged at a specified focal position inside the living organism A. Fluorescence generated inside the living organism A in response to the laser light irradiation returns via the objective optical system 3, the imaging optical system 20, the pupil projection optical system 19, the optical scanning unit 18, and the collimator optical system 17 and is propagated in the optical fiber 8. Then, after being converted to a collimated beam by the focusing lens 23 in the optical unit 7, the fluorescence is transmitted through the dichroic mirror 22 and is made incident on the photodetector 6 by the focusing lens 24. A fluorescence image acquired by the photodetector 6 is displayed on the monitor 26 connected to the photodetector 6.

With this configuration, the operator can obtain a clear fluorescence image focused on the examination site by operating the linear motion mechanism 31 while viewing the fluorescence image displayed on the monitor 26.

When the fluorescence emitted by the living organism A is focused onto the incident surface of the optical fiber 8, the core of the optical fiber 8 exhibits a pinhole effect, which eliminates blurring of the fluorescence image, thus improving the resolution in the optical axis direction. In other words, since only an in-focus image is produced, only an image near the optical axis is observed simply by slightly tilting the living organism A from the state orthogonal to the optical axis. Thus, by operating the rotation mechanism 9 to perform correction such that the optical axis C2 of the measurement head 4 is perpendicular to the living organism A, it is possible to obtain images that are in-focus over the entire field.

The in-vivo examination apparatus 1 of this embodiment is designed so that the rotating arm 30 rotates about the horizontal rotation axis C1, which is disposed so as to intersect the examination site. Therefore, by rotating the rotating arm 30, it is possible to examine the same examination site from a plurality of different angles within a vertical plane. In this case, since this is achieved simply by rotating the rotating arm 30 to which the measurement head 4 is fixed, it is possible to perform examination from various directions.

Also, since the in-vivo examination apparatus 1 of this embodiment is formed of the transparent part 10 at the position where the living organism A is mounted at the center of the stage 2, it is possible to examine the living organism A from underneath. If the living organism A is sufficiently thin, the measurement head 4 is disposed at the position indicated by the dotted line in FIG. 2 simply by rotating the rotating arm 30, and it is possible to examine the same examination site of the living organism A from both above and below. If the living organism is comparatively thick, various examination sites on the upper and lower sides of the living organism A can be selected, without moving the living organism A on the stage 2, and examination can be carried out from various angles.

Figure 3:
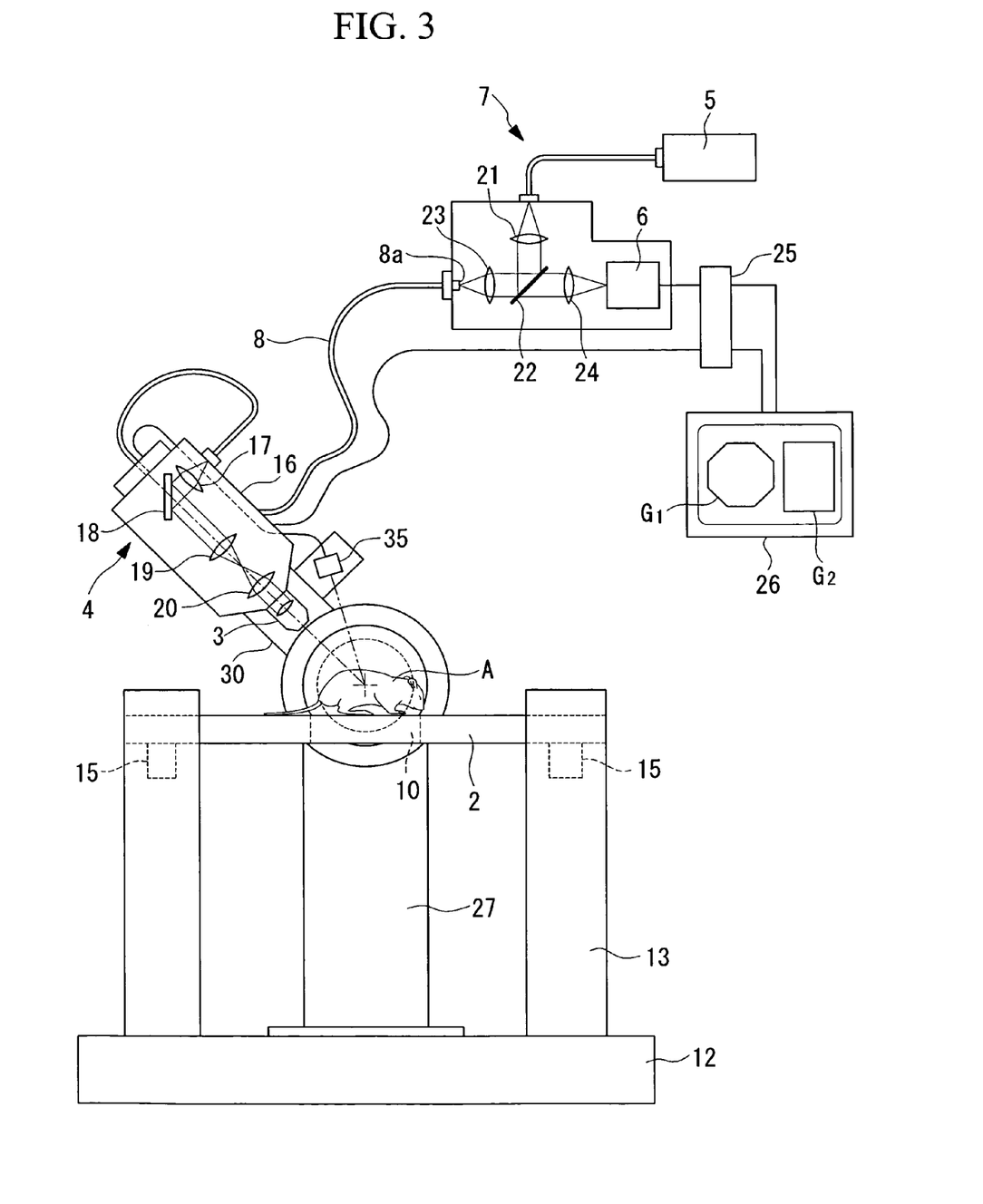
FIG. 3 is a front elevation view showing a modification of the in-vivo examination apparatus in FIG. 1.

As shown in FIG. 3, in the in-vivo examination apparatus of this embodiment, another imaging device, like a CCD camera 35, may be provided on the rotating arm 30. For example, by selecting a device with a low magnification as the CCD camera 35, it is possible to simultaneously examine the fluorescence image of the interior of the living organism A obtained by the measurement head 4 while imaging the surface of the living organism A with the CCD camera 35. In this case, as shown in FIG. 3 for example, a fluorescence image G1 acquired by the measurement head 4 and an image G2 of the surface of the living organism 4 are simultaneously displayed on the monitor 26, which allows the condition inside the living organism A and the corresponding condition at the surface of the living organism A to be examined simultaneously.

Figure 4:
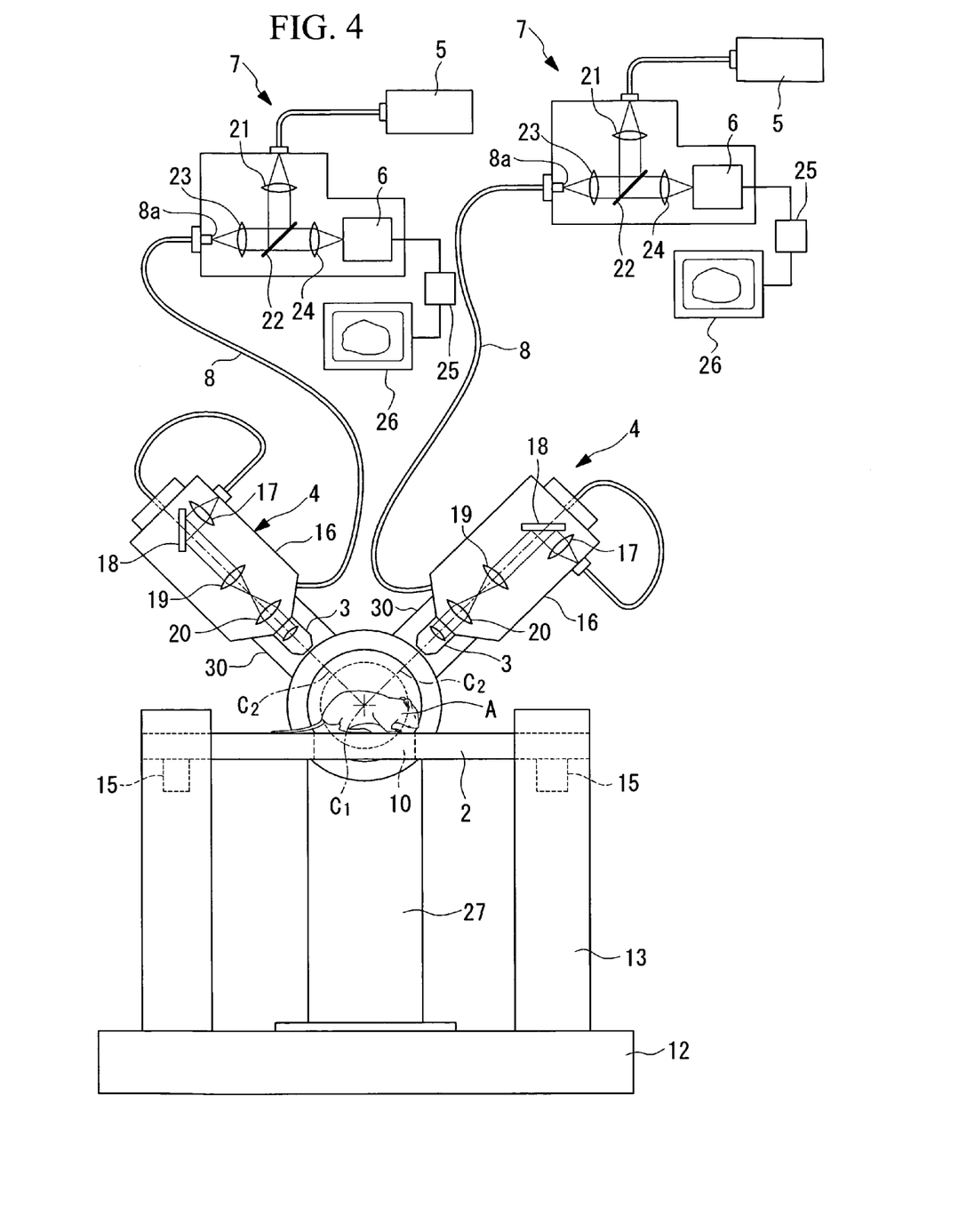
FIG. 4 is a front elevation view showing another modification of the in-vivo examination apparatus in FIG. 1.

Also, as shown in FIG. 4, a plurality of rotating arms 30, which are rotated about the same horizontal rotating axis C1, may be provided, and a measurement head 4 may be provided on each rotating arm 30. In addition to the case where the rotating arms 30 are rotated independently, they may also be rotated together with a fixed angular relationship therebetween. By configuring the apparatus in this way, it is possible to obtain fluorescence images of the same examination site from two different directions simultaneously, which allows more accurate examination of the conditions at the examination site.

Figure 5:
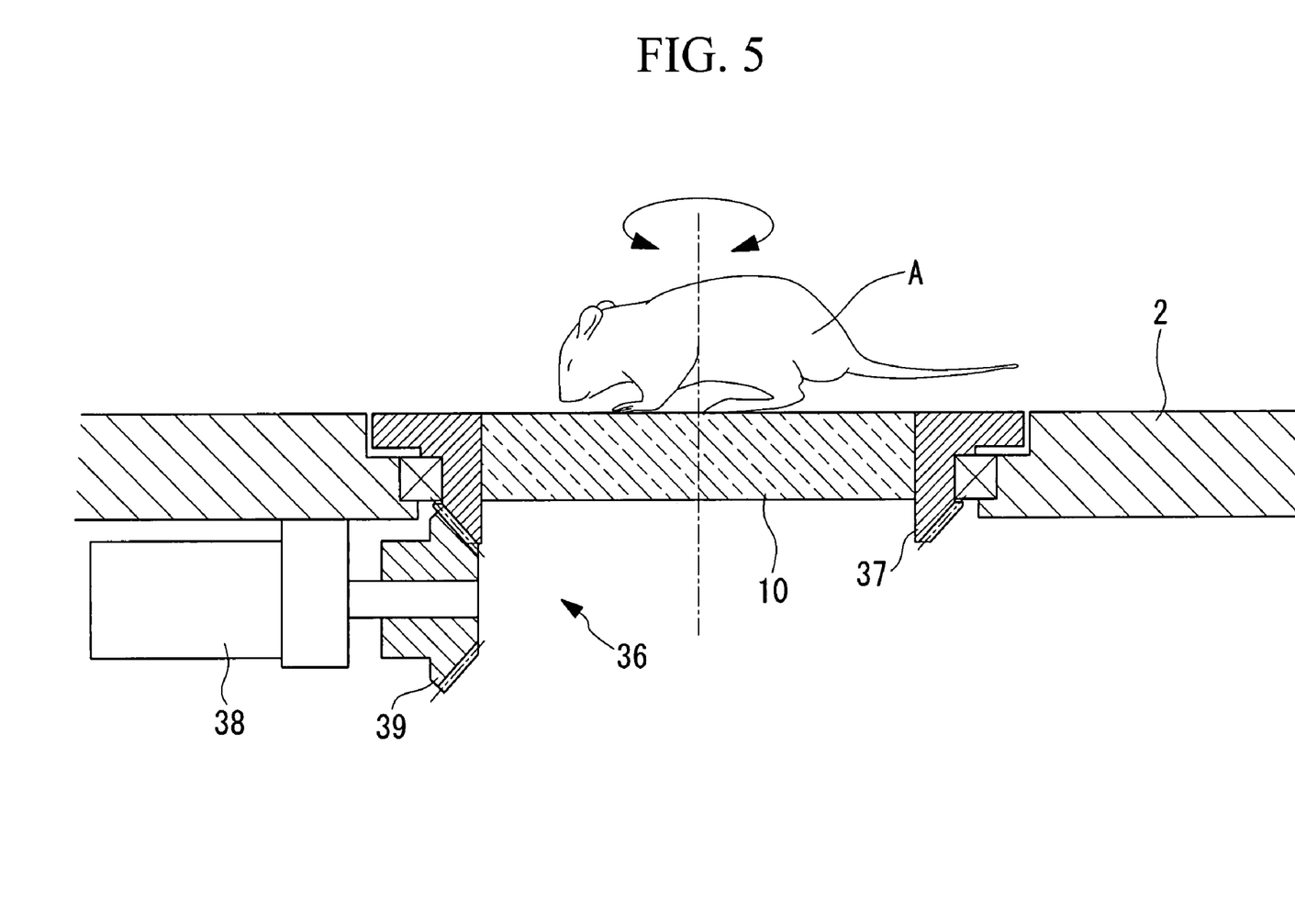
FIG. 5 is a longitudinal sectional view showing a modification of the stage of the in-vivo examination apparatus in FIG. 1.

Furthermore, as shown in FIG. 5, the in-vivo examination apparatus 1 of this embodiment may also be provided with a stage rotating mechanism 36 for rotating the stage 2 about a vertical axis. The stage rotating mechanism 36 includes, for example, a first ring-shaped gear 37 that supports the transparent part 10, a motor 38, and a second gear 39 that meshes with the first gear 37 and that is fixed to the motor 38. By configuring the apparatus in this way, the examination angle can be varied within the vertical plane by rotating the rotating arm 30, and the examination angle can be varied in the horizontal direction by rotating the stage 2. Therefore, the examination site of the living organism A secured to the stage 2 can be examined from any angle.

The stage 2 may also include a horizontal moving mechanism (not shown) for horizontally moving the living organism secured to the stage 2. By doing so, examination of different locations in the living organism A can be carried out while changing the examination angle.

SECOND EMBODIMENT

Next, an in-vivo examination apparatus 40 according to a second embodiment of the present invention is described below with reference to FIG. 6.

In the description of this embodiment, parts having the same structure as those in the in-vivo examination apparatus 1 according to the first embodiment described above are assigned the same reference numerals, and a description thereof is omitted.

Figure 6:
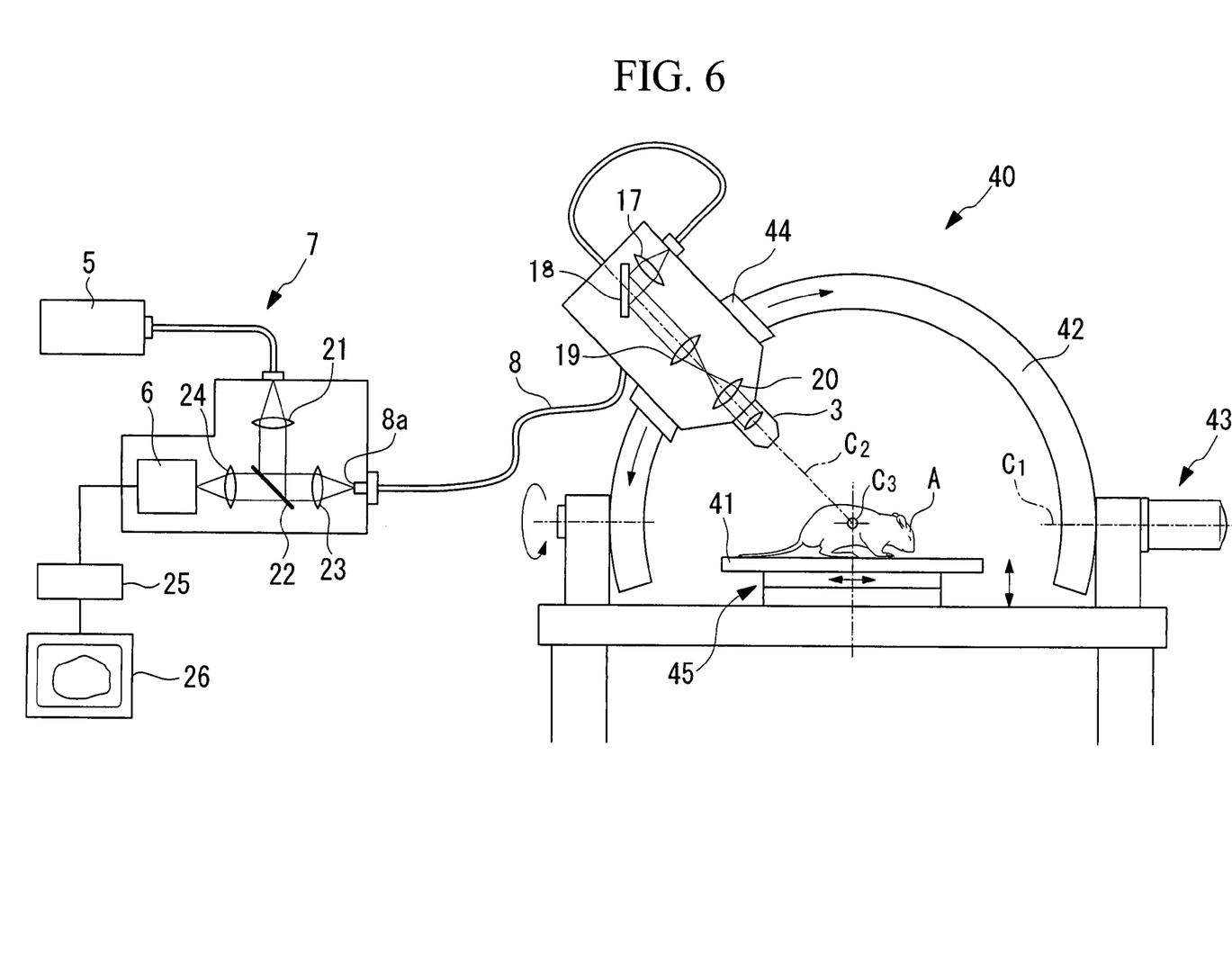
FIG. 6 is a front elevation view showing an in-vivo examination apparatus according to a second embodiment of the present invention.

As shown in FIG. 6, the in-vivo examination apparatus 40 of this embodiment differs from the in-vivo examination apparatus 1 of the first embodiment in that, instead of the rotating arm 30, an arc-shaped track member 42 is provided so as to be centered on an examination site located above the stage 41.

The arc-shaped track member 42 includes a track rotating mechanism 43 that makes the arc-shaped track member 42 rotate about a horizontal axis C1 extending in the radial direction thereof.

Also, a slider 44 that is moveable in the circumferential direction of the arc-shaped track member 42 is provided on the arc-shaped track member 42. The slider 44 is adapted so as to advance on the arc-shaped track member 42 by a driving mechanism such as a motor (not shown).

The measurement head 4 is attached to the slider 44 such that the optical axis C2 thereof passes through the center of the arc-shaped track member 42. By doing so, the optical axis C2 of the measurement head 4 can be made to always pass through the same position at the examination site, regardless of the motion of the slider 44 and rotation of arc-shaped track member 42. Also, since the motion of the slider 44 on the arc-shaped track member 42 and the rotation of the arc-shaped track member 42 are about mutually orthogonal axes C1 and C3, it is possible to carry out examination of the examination site of the living organism A from any direction with a certain combination of these motions.

Therefore, in this embodiment, the stage 41 on which the living organism A is mounted need not be rotated about a vertical axis. In this embodiment, as shown in FIG. 6, a moving mechanism 45 for moving the living organism A in the horizontal and vertical directions with respect to the intersection of the optical axis C2 of the measurement head 4, the central axis C3 of the arc-shaped track member 42, and the rotation axis C1 of the track rotating mechanism 43 is provided on the stage 41. Also, a linear motion mechanism (not shown) for moving the measurement head 4 in the radial direction is provided on the slider 44.

The operation of the in-vivo examination apparatus 40 according to this embodiment, with such a configuration, will be described below.

With the in-vivo examination apparatus 40 according to this embodiment, the track rotating mechanism 43 is fixed and the slider 44 is moved along the arc-shaped track member 42, thereby allowing the measurement head 4 to move within a plane intersecting a specified examination site in the living organism A. At this time, by operating the linear motion mechanism-provided on the slider 44, it is possible to locate the focal position of the measurement head 4 so as to be coincident with the examination site. Then, by operating the track rotating mechanism 43 while the focal position of the measurement head 4 is coincident with the examination site, the angle of the measurement head 4 with respect to the examination site can be varied while keeping the focal position on the examination site.

In other words, by operating the track rotating mechanism 43, which rotates the arc-shaped track member 42, the measurement head 4 can be rotated about the horizontal axis C1 together with the arc-shaped track member 42. Thus, by combining the rotation along the arc-shaped track member 42 and rotation of the arc-shaped track member 42 itself, it is possible to position the measurement head 4 at any orientation with respect to the living organism A, which allows examination of the living organism A from any angle.

In this case, enabling upward and downward movement and horizontal movement of the stage 41 on which the living organism A is mounted allows a desired examination site of the living organism A to be made coincident with the center of rotation of the measurement head 4.

THIRD EMBODIMENT

An in-vivo examination apparatus according to a third embodiment of the present invention is described below with reference to FIG. 7 and FIG. 8.

Figure 7:
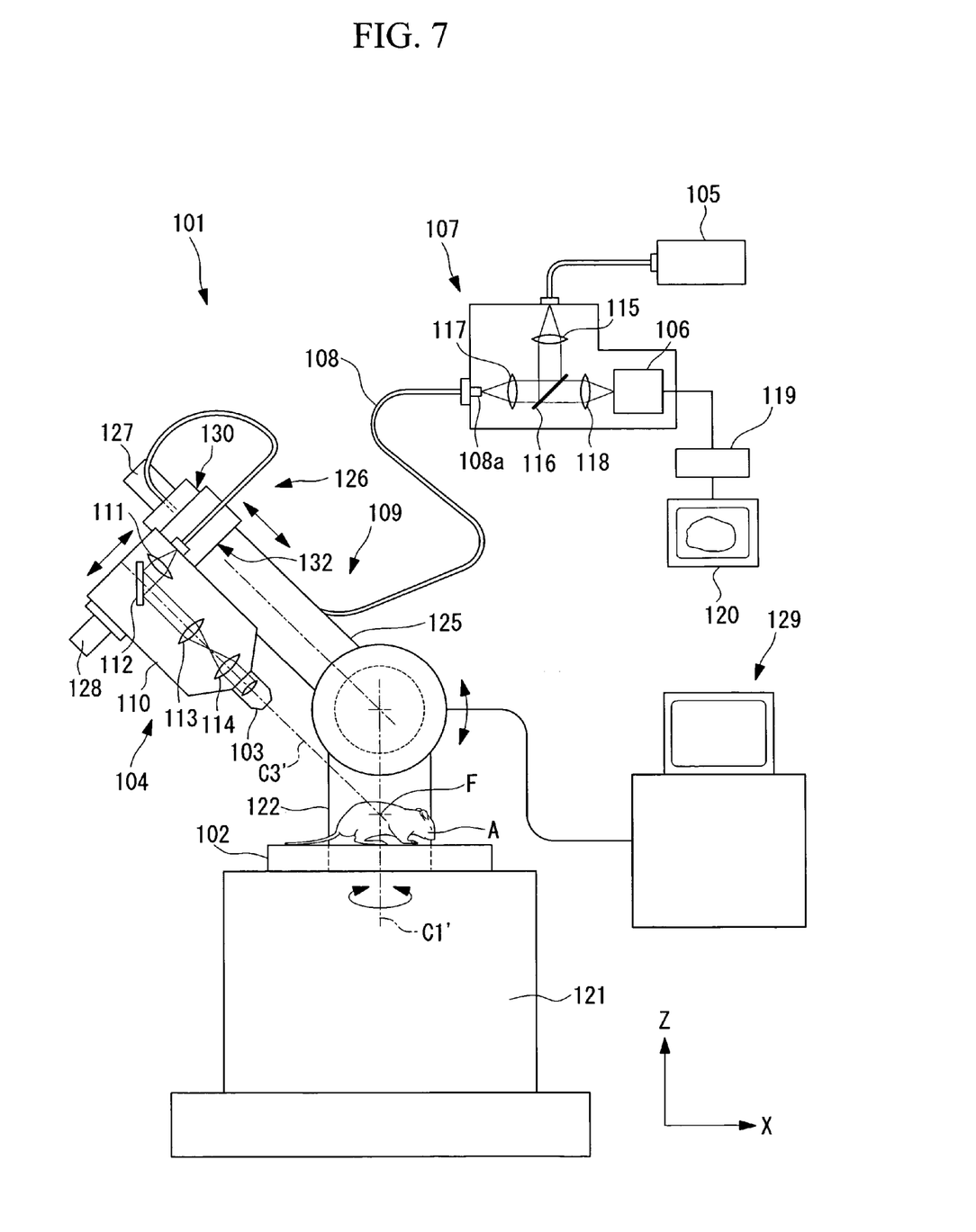
FIG. 7 is a front elevation view showing an in-vivo examination apparatus according to a third embodiment of the present invention.
Figure 8:
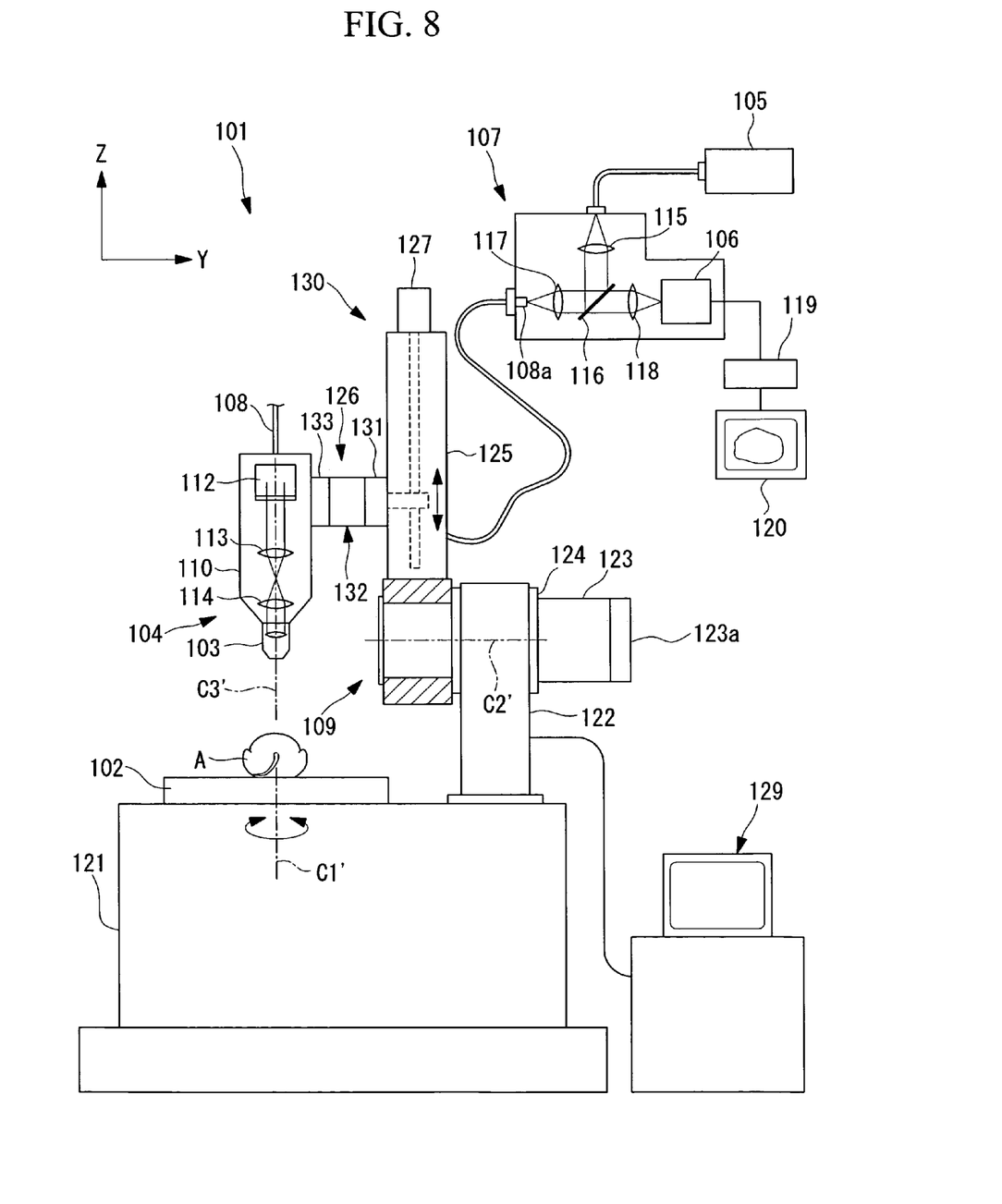
FIG. 8 is a side view of the in-vivo examination apparatus in FIG. 7.

As shown in FIGS. 7 and 8, an in-vivo examination apparatus 101 of this embodiment includes a stage 102 on which a living organism A is mounted; a measurement head 104 having an objective optical system (objective lens) 103 disposed at the end thereof; an optical unit 107 including a light source 105 and a photodetector 106; an optical fiber 108 that connects the measurement head 104 and the optical unit 107; and a rotation mechanism 109 for rotating the measurement head 104.

The stage 102 is disposed horizontally and can be rotated about a vertical axis C1.

The measurement head 104 includes a collimator optical system 111, an optical scanning unit 112, a pupil projection optical system 113, and an imaging optical system 114 inside a casing 110, which has the objective optical system 103 at the end thereof. The collimator optical system 111 converts laser light conveyed by the optical fiber 108 into a collimated beam. As shown schematically in the figure, the optical scanning unit 112 can two-dimensionally scan the collimated beam from the collimator optical system 11 by, for example, oscillating two galvano mirrors about two respective orthogonal axes.

The pupil projection optical system 113 focuses the laser light scanned by the optical scanning unit 112 to form an intermediate image. The imaging optical system 114 focuses the laser light forming the intermediate image to convert it to a collimated beam.

The objective optical system 103 is disposed close to the living organism A mounted on the stage 102, and focuses the collimated beam from the imaging optical system 114 to re-image it at a specified focal position F on the surface of the living organism A or inside the living organism A.

The optical unit 107 includes a collimator lens 115 for converting the laser light emitted from the laser light source 105 into a collimated beam; a dichroic mirror 116 that reflects the laser light and transmits return light returning from the optical unit 107; a focusing lens 117 that focuses the laser light reflected by the dichroic mirror 116 onto an end face 108a of the optical fiber 108; and a focusing lens 118 that focuses the return light transmitted through the dichroic mirror 116 onto the photodetector 106. The photodetector 106 is, for example, a photomultiplier tube. A monitor 120 is connected to the photodetector 106 via an image processing apparatus 119, and acquired images are displayed on the monitor 120.

The optical fiber 108 connects the optical unit 107 and the measurement head 104, carries the laser light emitted from the optical unit 107 to introduce it to the measurement head 104, and carries return light returning from the measurement head 104 to introduce it to the optical unit 107. As shown in FIG. 7, the optical fiber 108 is guided inside a rotating arm 125 (described later) towards the inner side in the longitudinal direction and is lead out from close to the center of rotation of the rotating arm 125 to be connected to the external optical unit 107.

A rotation mechanism 109 includes a support member 122 that is secured to a base 121; a motor 123 and a gear 124 that are secured to the support member 122; the rotating arm 125, which is secured to the gear 124; a two-axis linear motion mechanism 126 that translates the measurement head 104 in the longitudinal direction of the rotating arm 125 and in the direction orthogonal thereto, within a plane orthogonal to the rotation axis C2' of the rotating arm 125; and a control apparatus 129 that controls the operation of the motor 123 of the rotating arm 125 and motors 127 and 128 of the driving mechanism 126. The motor 123 and the gear 124 are secured to the support member 122 with the rotation axis C2' thereof placed horizontally. A rotation angle sensor 123a for detecting the rotation angle of the rotating arm 125 is provided on the motor 123, and the output thereof is conveyed to the control apparatus 129.

The linear motion mechanism 126 includes a first linear guide 130 that is fixed along the longitudinal direction of the rotating arm 125; a first slider 131 that is supported so as to be translatable in the longitudinal direction of the rotating arm 125 via the first linear guide 130; a first motor 127 that drives the first linear guide 130; a second linear guide 132 that is fixed to the first slider 131; a second slider 133 that is supported so as to be translatable in a direction orthogonal to the longitudinal direction of the rotating arm 125 and the rotating axis C2' via the second linear guide 132; and a second motor 128 for driving the second linear guide 132.

The first and second linear guides 130 and 132 include linear motion apparatuses like ball screws. The measurement head 104 is fixed to the slider 133 so that the optical axis C3' of the objective optical system 103 thereof is positioned parallel to the longitudinal direction of the rotating arm 125.

The control apparatus performs control so as to engage the motor 123 of the rotating arm 125, which together constitute the rotation mechanism 109, and the first and second motors 127 and 128 of the linear motion mechanism 126. More concretely, when varying the examination direction with respect to the examination site when the focal position F of the objective optical system 103 of the measurement head 104 is coincident with the examination site of the living organism A, upon operating the motor 123 to rotate the rotating arm 125 about a horizontal axis, the output of the rotation angle sensor 123a in the motor 123 is sent to the control apparatus 129. Then, the control apparatus 129 rotates the measurement head 104 with the focal position of the objective optical system 103 as the center of rotation, by engaging and operating the first motor 127 and the second motor 128.

For example, when the motor 123 is operated to rotate the rotating arm 125 by an angle $\theta$, the angle $\theta$ of the rotating arm 125 is detected by the rotation angle sensor 123a. Then, the control apparatus 129 moves the measurement head 104 by distance $R(1-\cos\theta)$ in the longitudinal direction of the rotating arm 125 via the first linear guide 130, and moves the measurement head 104 by distance $R(\sin\theta)$ in a direction orthogonal to the longitudinal direction of the rotating arm 125 via the second linear guide 132, where R is defined as the distance between the rotation axis C2' of the rotating arm 125 and the focal position F of the objective optical system 103.

The operation of the in-vivo examination apparatus 101 according to this embodiment, having such a configuration, will be described below.

To carry out in-vivo examination of the living organism A using the in-vivo examination apparatus 101 of this embodiment, as shown in FIG. 7, the living organism A is secured to the stage 102. Then, by operating the first motor 127 of the linear motion mechanism 126 attached to the rotating arm 125, the measurement head 104 is moved in the radial direction parallel to the longitudinal direction of the rotating arm 125. By doing so, since it is possible to secure a sufficiently large space around the stage 102, it is easy to set the living organism A in place.

Next, by operating the rotation mechanism 109, the rotating arm 125 and the measurement head 104 attached to the rotating arm 125 are rotated about the rotation axis C2'. By doing so, the tilt angle of the optical axis C3' of the measurement head 104 is varied within a vertical plane, which allows the examination angle to be set as desired. In this state, by operating the linear motion mechanism 126, which is attached to the rotating arm 125, the measurement head 104 is moved in the longitudinal direction of the rotating arm 125 to adjust the distance between the living organism A and the objective optical system 103 at the end of the measurement head 104.

After setting it roughly by visual observation, the distance between the living organism A and the objective optical system 103 is set by moving the optical unit 107 while looking at the monitor 120.

When the optical unit is operated to emit laser light from the laser light source 105, the emitted laser light passes through the collimator lens 115, the dichroic mirror 116, and the focusing lens 117 to be focused onto the end face 108a of the optical fiber 108 and introduced into the optical fiber 108. Then the laser light introduced into the optical fiber 108 propagates in the optical fiber to be guided to the measurement head 104. The laser light then passes through the collimator optical system 111, the optical scanning unit 112, the pupil projection optical system 113, the imaging optical system 114, and the objective optical system 103 to be imaged at a specified focal position F inside the living organism A.

Fluorescence produced in the interior of the living organism A in response to laser irradiation returns through the objective optical system 103, the imaging optical system 114, the pupil projection optical system 113, the optical scanning unit 112, and the collimator optical system 111, and propagates through the optical fiber 108. Then, after being converted to a collimated beam by the focusing lens 117 in the optical unit 107, the fluorescence is transmitted through the dichroic mirror 116 and is made incident on the photodetector 106 by the focusing lens 118. The fluorescence image acquired by the photodetector 106 is displayed on the monitor 120, which is connected to the photodetector 106.

Accordingly, by operating the linear motion mechanism 126 while the operator views the fluorescence image displayed on the monitor 126, the focal position F can be adjusted to the examination site and a clear fluorescence image can be obtained.

When the fluorescence produced by the living organism A is focused on the incident surface of the optical fiber 108, the core of the optical fiber 108 provides a pinhole effect that cuts out blurring in the fluorescence image, which improves the resolution in the optical axis direction. In other words, since only an in-focus image is produced, only an image near the optical axis is observed simply by slightly tilting the living organism A from a state orthogonal to the optical axis. Thus, by operating the rotation mechanism 109 to perform correction such that the optical axis C3' of the measurement head 104 is perpendicular to the living organism A, it is possible to obtain images that are in-focus over the entire image.

When it is desired to examine the same examination site from different directions when the focal position F of the objective optical system 103 is coincident with the examination site of the living organism A, the rotating arm 125 is rotated about the horizontal rotation axis C2' while the control apparatus 129 is operated. Since the measurement head 104 is fixed to the linear motion mechanism 126 mounted on the rotating arm 125, rotating the rotating arm 125 causes measurement head 104 to be inclined at the same inclination angle as the inclination angle of the rotating arm 125. Also, in this embodiment, since the control apparatus 129 operates the two-axis linear motion mechanism 126 in conjunction with the rotation of the rotating arm 125, the measurement head 104 is made to rotate about the focal position F of the objective optical system 103. Therefore, it is possible to examine the living organism A from various directions within the X-Z plane in FIG. 7, while keeping the focal position F of the objective optical system 103 fixed at the same examination site.

In addition, with the in-vivo examination apparatus 101 according to this embodiment, when the examination site is not positioned on the rotation axis C2' of the rotating arm 125, rotating only the rotating arm 125 causes the focal position F of the measurement head 104 to become misaligned from the examination site; however, engaging the two-axis linear motion mechanism 126 by operating the control apparatus 129 allows the misalignment to be corrected, which maintains the state where the focal position F of the objective optical system 103 is coincident with the same examination site even during rotation of the rotating arm 125. Therefore, when securing the living organism A to the stage 102, it can be set in place more easily since there is no need to align the rotation axis C2' of the rotating arm 125 so that it intersects the examination site of the living organism A.

In the in-vivo examination apparatus according to this embodiment, since the stage 102 on which the living organism A is mounted is rotated about the vertical axis C1', it is possible to make the X-Z plane, in which the optical axis C3' of the measurement head 104 lies, intersect with different cross-sectional planes of the living organism A by rotating the stage 102, on which the living organism A is secured, about the vertical axis C1'.

Figure 9:
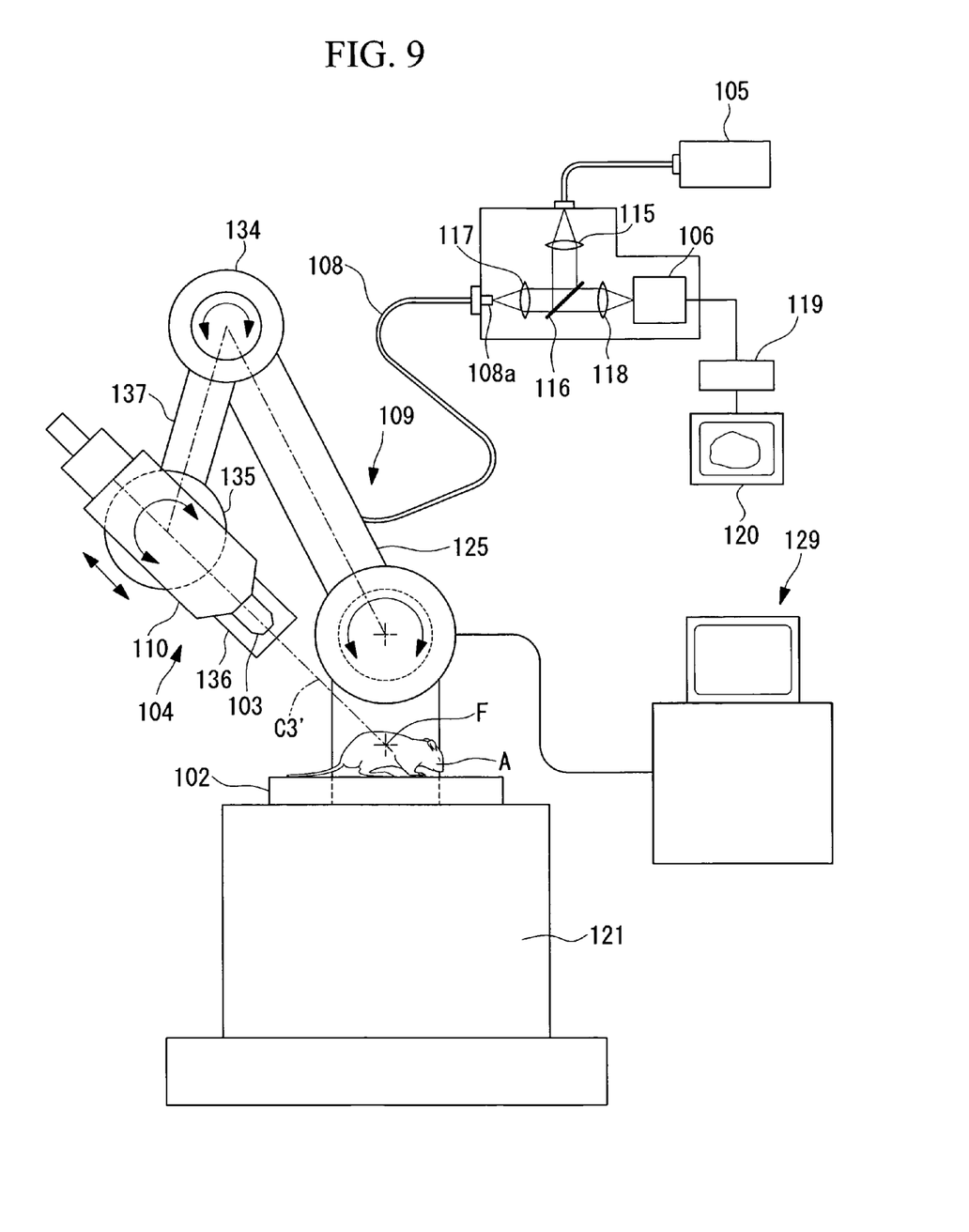
FIG. 9 is a front elevation view of a modification of the in-vivo examination apparatus in FIG. 7.

In the in-vivo examination apparatus 101 according to this embodiment, the two-axis linear motion mechanism 126 is installed on the rotating arm 125; however, instead of this, as shown in FIG. 9, another two rotation shafts 134 and 135 and one linear motion mechanism 136 may be installed on the rotating arm 125. By configuring the system in this way, rotating the rotating arm 125 together with the second rotating arm 137 allows the direction of the optical axis C3' of the measurement head 104 to be set by specifying the position of the end of the second rotating arm 137 and rotating the rotation shaft 135 at the end of the second rotating arm 137. Then, by operating the linear motion mechanism 136, the measurement head 104 can be moved in the direction of the optical axis C3' thereof. In the same way, the angle of the measurement head 104 can be varied while keeping the focal position F of the objective optical system 103 fixed.

Figure 10:
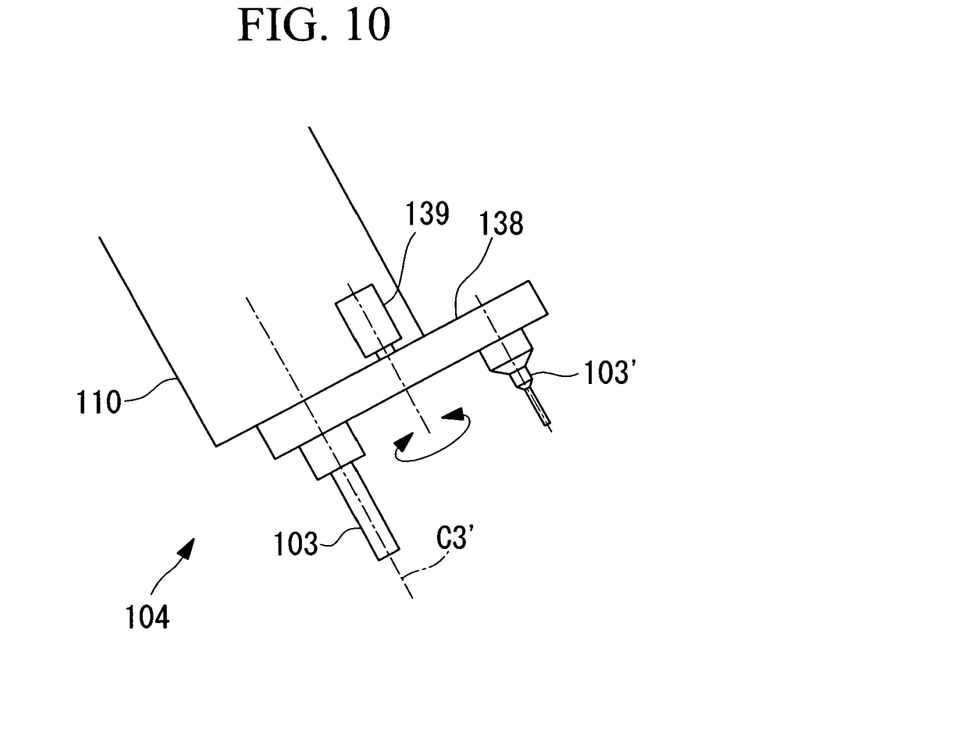
FIG. 10 is a front elevation view showing an objective switching mechanism attached to the end of the measurement head of the in-vivo examination apparatus in FIG. 7.

As shown in FIG. 10, multiple objective lens optical systems 103 and 103' with different magnifications can be attached to the end of the measurement head 104 in such a manner that the apparatus can switch between them. In the example shown in FIG. 10, multiple objective optical systems 103 and 103' are fixed on a turret 138 that is rotatably attached to the end of the casing 110 of the measurement head 104. By operating a motor 139, the turret 138 rotates and one of the objective optical systems 103 and 103' is selectively disposed in the optical axis C3', which allows examination to be carried out with different magnifications.

Figure 11:
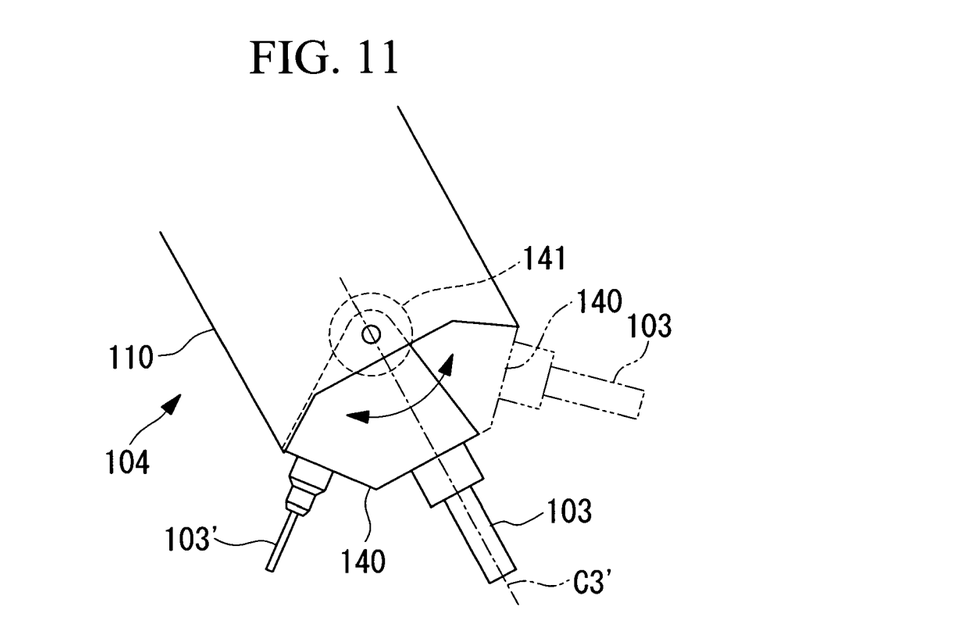
FIG. 11 is a front elevation view showing another objective switching mechanism attached to the end of the measurement head of the in-vivo examination apparatus in FIG. 7.

As shown in FIG. 11, as the mechanism for allowing the objective optical systems 103 and 103' to be switched, the multiple objective optical systems 103 and 103' with different magnifications may be fixed to rocking member that is attached to the end of the casing 110 of the measurement head 104 so as to be rockable. By operating a motor 141 to rock the rocking member 140, one of the objective optical systems 103 and 103' can be selectively positioned in the optical axis C3', which allows examination to be carried out with different magnifications.

In the cases described above, since the focal position F is different for each of the objective optical systems 103 and 103', when the objective optical systems 103 and 103' are switched, the control apparatus 129 reads out information on the objective optical system 103 or 103' positioned on the optical axis C3' and changes the driving direction of the rotation mechanism 109 in response thereto.

According to a first aspect, the present invention provides an in-vivo examination apparatus including a stage on which a living organism is mounted; a measurement head that irradiates the living organism on the stage with light emitted from a light source; and a rotation mechanism that rotates the measurement head about a fixed point on the stage.

With this configuration, it is possible to examine the living organism by focusing the measurement head on the living organism mounted on the stage, irradiating the living organism with light emitted from the light source, and detecting light returning from the living organism. In this case, the examination site of the living organism and the focal position of the measurement head are disposed at a point serving as the center of rotation of the measurement head by the rotation mechanism. In this state, by operating the rotation mechanism to rotate the measurement head with respect to the stage, it is possible to examine the living organism from different directions. Accordingly, during rotation, since the measurement head rotates about the focal position, the viewing angle can be changed while keeping the examination site at the focal point.

When the rotation mechanism is operated to position the measurement head below the stage, it is possible to easily detect the irradiation and return light of the light for the living organism from the measurement head because the stage is made of transparent material.

In the above-described aspect, the rotation mechanism preferably includes a rotating arm that is rotatable about a horizontal axis, and wherein a driving mechanism for moving the measurement head along the radial direction may be provided on the rotating arm.

With this configuration, by fixing the linear motion mechanism and operating the rotating arm, it is possible to vary the examination angle of the living organism within a single vertical plane. Also, by fixing the rotating arm and operating the linear motion mechanism, it is possible to change the distance between the measurement head and the living organism. Therefore, when manipulating the living organism on the stage, operating the linear motion mechanism allows the measurement head to be removed from the vicinity of the stage to ensure sufficient working space, and it is possible to bring the measurement head close to the living organism when carrying out examination by operating the linear motion mechanism.

The invention according to the above-described aspect may also include a stage rotating mechanism for rotating the stage about a vertical axis.

With this configuration, operating the stage rotating mechanism allows the living organism to be rotated within a horizontal plane. Therefore, particularly in combination with the rotating arm whose examination angle with respect to the living organism can be adjusted within a vertical plane, it is possible to examine the living organism from all directions.

The invention according to the above-described aspect may also include a stage raising/lowering mechanism for raising and lowering the stage in the vertical direction. By operating the stage raising/lowering mechanism, the site to be examined in the living organism can be positioned at the center of rotation of the rotation mechanism.

In the above-described aspect, the rotation mechanism may include an arc-shaped track centered on the focal position, and a slider that is moveable along the arc-shaped track. The measurement head may be attached to the slider.

By moving the slider along the arc-shaped track, the measurement head is rotated about a fixed point on the stage, and it is possible to examine the living organism from different directions.

The above-described aspect of the invention may also include a track rotating mechanism that rotates the arc-shaped track about a horizontal axis passing through a focal position of the measurement head.

With this configuration, it is possible to set the arc-shaped track at various angles with respect to the living organism, which allows examination of the examination site in the living organism from any angle.

The invention according to the above-described aspect may also include an externally provided light source, and an optical fiber for carrying light emitted from the light source to the measurement head. In addition, the measurement head may include an optical scanning unit for scanning the light from the light source and an objective optical system that images the light scanned by the optical scanning unit onto the stage.

By disposing the light source externally, it is possible to make the measurement head more compact. Also, by connecting the light source and the measurement head with the optical fiber, it is possible to place the measurement head at any orientation and position in the vicinity of the living organism by bending the optical fiber.

In the above-described aspect, the fixed point is preferably arranged so as to be coincident with the focal position. Also, the stage is preferably moveable horizontally.

According to the first aspect of the invention, the measurement head can be rotated with respect to the living organism on the stage to allow examination from any direction. Also, since the examination angle is set with the measurement head using only the rotation mechanism, the examination direction can be changed while maintaining the accuracy of the examination site. Furthermore, since the examination angle is set with the measurement head using only the rotation mechanism, once the examination angle is set, an advantage is afforded in that it is possible to perform re-examination from the same angle with high accuracy.

According to a second aspect, the present invention provides an in-vivo examination apparatus including a stage on which a living organism is mounted; a measurement head having an objective lens that irradiates the living organism on the stage with light emitted from a light source, and that receives return light from the living organism; and a rotation mechanism that rotates the measurement head about a horizontal axis centered on a focal position of the objective lens. The rotation mechanism has at least three operating axes in a plurality of directions, in which the measurement head can move, and a control apparatus for engaging these operating axes.

According to this aspect, examination of a living organism can be carried out by focusing the objective lens at the end of the measurement head on the living organism mounted on the stage, irradiating the living organism with light emitted from the light source, and detecting light returning from the living organism. Then, to examine the living organism from different directions, the measurement head is rotated about the focal position of the objective lens by operating the rotation mechanism. Therefore, it is possible to change the viewing angle of the living organism while keeping the examination site in focus.

In this case, since the control apparatus drives three or more operating axes, it is possible to change the angle of the measurement head within a vertical plane without moving the focal position thereof, regardless of which point the focal position of the objective lens is set to. Therefore, securing the living organism to the stage can be performed simply, without the need to consider the focal position.

In the above-described aspect, the rotation mechanism preferably includes a rotating member that rotates about a horizontal axis away from the focal position of the objective lens; and a two-axis linear motion mechanism that can move the measurement head, which is attached to the rotating member, in two mutually orthogonal directions within a plane perpendicular to the rotating member. In addition, the control apparatus may control the two-axis linear motion mechanism in response to a rotation angle of the rotating member.

By rotating the rotating member about a horizontal axis away from the focal position of the objective lens, any misalignment in the focal position of the objective lens can be corrected by operating the two-axis linear motion mechanism, and the angle of the measurement head can be changed within a vertical plane while keeping the focal position of the objective lens fixed. Reducing the number of rotation axes and performing correction with the linear motion axes allows the focal position to be fixed with better accuracy.

In the above-described aspect, the stage may be arranged so as to be rotatable about a vertical axis that intersects the focal position of the objective lens. By rotating the stage about a vertical axis, it is possible to rotate the measurement head within different vertical planes with respect to the living organism, which allows the examination region to be widened further.

In the above-described aspect, the measurement head may include an objective switching mechanism for switching between a plurality of objective lenses with different focal positions. In addition, the control apparatus may engage the operating axis based on information of the focal position of the objective lens, which is obtained from the objective switching mechanism.

By doing so, it is possible to examine the same living organism with multiple objective lenses having different magnifications.

What is claimed is:

1. An in-vivo examination apparatus comprising:
   a stage on which a living organism is mounted;
   a measurement head that irradiates the living organism on the stage with light emitted from a light source; and
   a rotation mechanism that rotates the measurement head about a fixed point on the stage, wherein the rotation mechanism includes a rotating arm that is rotatable about a horizontal axis, and wherein a linear motion mechanism for moving the measurement head along a radial direction is provided on the rotating arm.

2. An in-vivo examination apparatus according to claim 1, wherein the rotation mechanism has an operating range such that the measurement head can be positioned above and below the stage.

3. An in-vivo examination apparatus according to claim 1, wherein the stage is formed of a transparent material.

4. An in-vivo examination apparatus according to claim 1, further comprising:
   a stage rotating mechanism for rotating the stage about a vertical axis.

5. An in-vivo examination apparatus according to claim 1, further comprising:
   a stage raising/lowering mechanism for raising and lowering the stage in a vertical direction.

6. An in-vivo examination apparatus according to claim 1, further comprising:
   an externally provided light source, and
   an optical fiber for carrying light emitted from the light source to the measurement head, wherein the measurement head includes an optical scanning unit for scanning the light from the light source and an objective optical system that images the light scanned by the optical scanning unit onto the stage.

7. An in-vivo examination apparatus according to claim 1, wherein the fixed point is formed so as to be coincident with a focal position.

8. An in-vivo examination apparatus according to claim 1, further comprising:
a horizontal moving mechanism for moving the stage horizontally.

* * * * *